US009227083B2

(12) United States Patent
Hastenteufel et al.

(10) Patent No.: US 9,227,083 B2
(45) Date of Patent: Jan. 5, 2016

(54) DEVICE AND METHOD FOR RADIATION DOSIMETRY

(71) Applicant: Siemens Aktiengesellschaft, München (DE)

(72) Inventors: Mark Hastenteufel, Heidelberg (DE); Iwan Kawrakow, Ljulin (BG); Christian Scholz, Ketsch (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/627,734

(22) Filed: Sep. 26, 2012

(65) Prior Publication Data

US 2013/0079579 A1 Mar. 28, 2013

(30) Foreign Application Priority Data

Sep. 26, 2011 (DE) .......................... 10 2011 083 414

(51) Int. Cl.
*G21K 5/04* (2006.01)
*A61N 5/10* (2006.01)

(52) U.S. Cl.
CPC ............... *A61N 5/10* (2013.01); *A61N 5/1031* (2013.01); *A61N 5/1065* (2013.01); *A61N 2005/1061* (2013.01); *A61N 2005/1074* (2013.01); *A61N 2005/1087* (2013.01)

(58) Field of Classification Search
USPC ................................. 250/492.1, 492.3; 600/1
See application file for complete search history.

(56) References Cited

U.S. PATENT DOCUMENTS

| 7,978,817 | B2 | 7/2011 | Rietzel | |
|---|---|---|---|---|
| 2005/0111621 | A1* | 5/2005 | Riker et al. | 378/65 |
| 2005/0218341 | A1* | 10/2005 | Saracen et al. | 250/491.1 |
| 2008/0219405 | A1* | 9/2008 | Falco et al. | 378/65 |
| 2012/0136677 | A1 | 5/2012 | Ziegenhein et al. | |
| 2013/0289332 | A1* | 10/2013 | Purdie et al. | 600/1 |

FOREIGN PATENT DOCUMENTS

| DE | 103 18 204 A1 | 11/2004 |
|---|---|---|
| DE | 10 2008 019 128 A1 | 10/2009 |
| DE | 10 2010 062 079 A1 | 8/2012 |
| EP | 2 260 902 A1 | 12/2010 |
| WO | WO 2004/093971 A3 | 11/2004 |
| WO | WO 2012/069999 A3 | 5/2012 |

OTHER PUBLICATIONS

German Office Action dated Aug. 4, 2012 for corresponding German Patent Application No. DE 10 2011 083 414.1 with English translation.

* cited by examiner

*Primary Examiner* — Nicole Ippolito
(74) *Attorney, Agent, or Firm* — Lempia Summerfield Katz LLC

(57) ABSTRACT

A method and a device for regulating a therapeutic beam directed at an object are provided. The method includes displaying at least one multidimensional image data record encompassing at least one target area of the object. The method also includes determining the treatment beam dosage directed at the at least one target area, and recording and optionally visualizing an isoline or isosurface dependent on the treatment beam dosage in the at least one multidimensional image data record. The method includes adjusting the isoline or isosurface such that the isoline or isosurface approximates a contour of the target area as closely as possible or corresponds to the contour, and regulating the treatment beam dosage by evaluation of the adjusted isoline or isosurface.

13 Claims, 3 Drawing Sheets

DEVICE AND METHOD FOR RADIATION DOSIMETRY

This application claims the benefit of DE 10 2011 083 414.1, filed on Sep. 26, 2011.

BACKGROUND

The present embodiments relate to a device and a method for regulating a radiation dose.

Radiation therapy includes irradiating diseased tissue with X-ray beams, electron beams or particle beams. For example, particle therapy has developed over the last few years into an established method for the treatment of tissue (e.g., tumorous diseases). However, irradiation methods, as deployed, for example, in particle therapy, may also be deployed in non-therapeutic areas such as, for example, the irradiation of phantoms or non-living bodies for the purposes of research work and/or during the irradiation of materials.

During particle therapy, particles are generated (e.g., ions such as protons, carbon ions or other types of ions). The particles are accelerated to high energies in an accelerator, formed into a particle beam and directed at the tissue to be irradiated. The particles penetrate the tissue to be irradiated where the particles discharge energy of the particles in a circumscribed region. The depth of penetration of the particle beam into the tissue to be irradiated is primarily a function of the energy of the particle beam. The greater the energy of the particle beam, the deeper the particles penetrate the tissue to be irradiated.

During the radiation therapy planning process, the total quantity of the radiation to be supplied by the irradiation device is to be defined. This may be expressed by a number of monitor units (MUs) for treatment with external electron or photon light beams or as ion pulse counters that count treatments with protons or heavy ions. The following explanation applies to MUs, but all the explanations below are also applicable to ion pulse counters.

A dose calculation algorithm in treatment planning software is calibrated to calculate one radiation dose per monitor unit D/MU to enable the prescription of an absolute dose that may be used to determine the required MU.

There are different options for determining the desired dose. The different options include, for example: dose at a reference point is X Gy, or the maximum dose is X Gy; or the average dose at a target area or volume is X Gy, or the dose of Y % of the maximum dose of isoline or isosurface is X Gy. If the dose distribution in the target area is not constant, dose coverage of the tumor is to be minimized. This may be the case with electron-beam treatments, with conventional treatments with photon light beams, with treatments with scanned particle light beams, with brachytherapy treatment, or with advanced treatment techniques such as, for example, intensity-modulated radiation therapy and radiosurgery. The renormalization of the dose may entail a repetitive, laborious and long-winded trial and error process when amending the prescribed dose or during the renormalization of the dose, and when observing changes in a specific isoline record.

SUMMARY AND DESCRIPTION

The present embodiments may obviate one or more of the drawbacks or limitations in the related art. For example, a device and a method for the performance of irradiation treatment with a particle beam facilitating flexibility and accuracy of a beam dosimetry are provided.

One embodiment of the method for regulating a therapeutic beam directed at an object includes displaying at least one multidimensional image data record encompassing at least one target area of the object. The method also includes determining a treatment beam dosage directed at the target area, and recording and optionally visualizing an isoline or isosurface dependent on the treatment beam dosage in the at least one multidimensional image data record. The method includes adjusting the isoline or isosurface such that the isoline or isosurface approximates a contour of the target area as closely as possible or corresponds to the contour. The treatment beam dosage is regulated by evaluation of the adjusted isoline or isosurface.

The adjustment may be performed automatically or manually via a user interface.

In one embodiment, the regulated treatment beam dosage lies within one or more limit values.

In another embodiment, the treatment beam dosage to be determined is preset or set automatically or manually via a user interface.

The following may also be provided: algorithms and methods for calculating, displaying or visualizing isolines/isosurfaces; user control elements in treatment planning software that control the isoline definition; automatic determination of the isoline/surface most closely approximating the shape of the target area (e.g., a tumor); and automatic or manual use of the normalization value derived from the previously determined definition of the isoline or the isosurface.

Advantages of the present embodiments include: suitable combination of the usable user control elements and the isoline/isosurface calculation and the visualization in order to achieve optimum dose coverage; and automatic calculation of the isolines best encompassing the target, where the process of absolute dose normalization is improved. As a result, the present embodiments facilitate faster and possibly more accurate absolute dose normalization during the radiation therapy planning process.

In one embodiment, a device for regulating a therapeutic beam directed at an object includes means or modules for performing the aforementioned method. The means or modules for performing the aforementioned method may be embodied in the form of hardware and/or software, or as a computer program product or a non-transitory computer readable storage medium that stores program code including instructions executable by the hardware.

The device may be implemented in a control unit (e.g., a processor), a computer or a server.

The at least one image data record and the isoline or isosurface may be visually displayed on a display device. A user interface (e.g., a mouse, keyboard, or touch screen) may be used to change the isoline or surface.

The device and the method may be developed further.

DETAILED DESCRIPTION OF THE DRAWINGS

Figure 1:
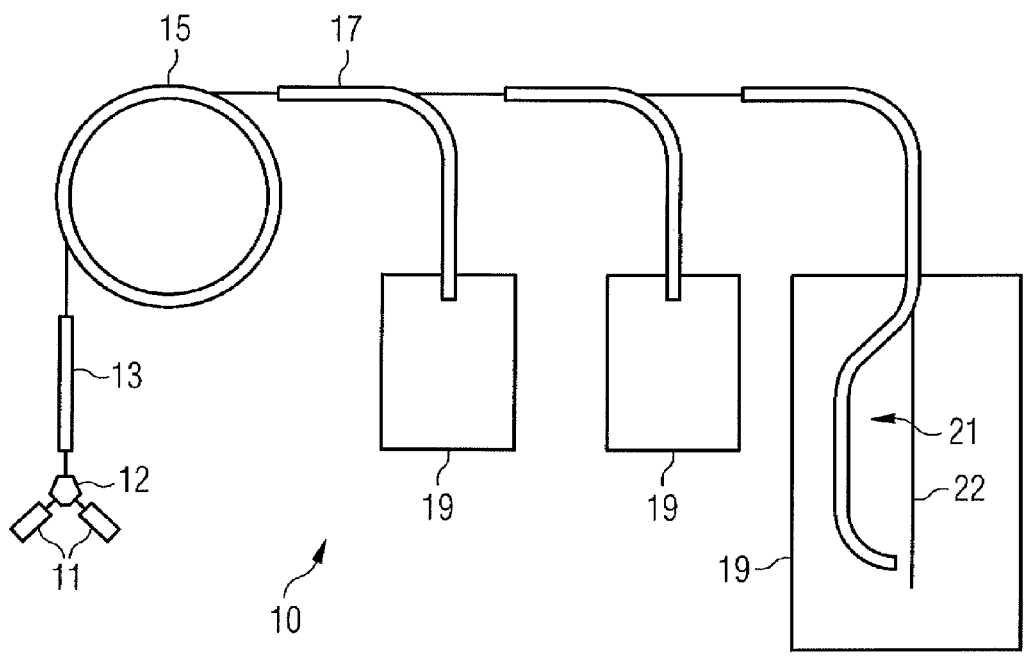
FIG. 1 shows a schematic diagram of a particle therapy system.
Figure 2:
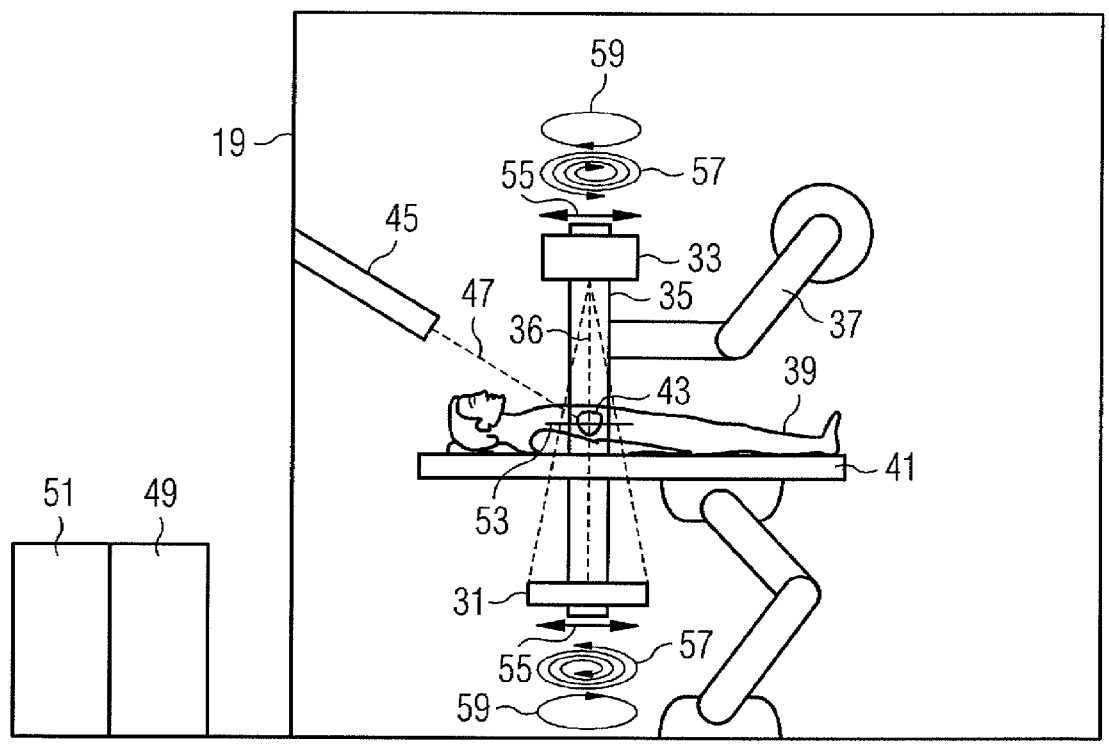
FIG. 2 shows an arrangement of a beam outlet and an imaging unit in an irradiation chamber.

FIGS. 1 and 2 are schematic diagrams of a particle therapy system and an arrangement of a beam outlet and imaging unit, respectively. The particle therapy system and the arrangement of the beam outlet and imaging unit are known, for example, from DE 10 2008 019 128 A1.

FIG. 1 is a schematic overview of a particle therapy system 10. The particle therapy system 10 is used, for example, for the irradiation of a body (e.g., tumorous tissue) using a particle beam.

The particles used may be ions such as, for example, protons, pions, helium ions, carbon ions or other types of ions. Particles of this type may be generated in a particle source 11. If, as shown in FIG. 1, there are two particle sources 11 that generate two different types of ion, the two types of ion may be switched between within a short time interval. This switching is performed, for example, by a switching magnet 12 that is disposed between the ion sources 11 and a preaccelerator 13. For example, this enables the particle therapy system 10 to be operated with protons and carbon ions at the same time.

The ions generated by the ion source or one of the ion sources 11 and optionally selected using the switching magnet 12 are accelerated to a first energy level in the preaccelerator 13. The preaccelerator 13 is, for example, a linear accelerator (LINAC: "LINear ACcelerator"). The particles are fed into an accelerator 15 (e.g., a synchrotron or cyclotron). In the accelerator 15, the particles are accelerated to high energies as required for the irradiation. Once the particles exit the accelerator 15, a high-energy beam transportation system 17 directs the particle beam to one or more irradiation chambers 19. In an irradiation chamber 19, the accelerated particles are directed at a body to be irradiated. Depending upon the embodiment, this is performed from a fixed direction (e.g., in "fixed beam" chambers) or from different directions by way of a rotatable gantry 21 that may be moved about an axis 22.

The structure of the particle therapy system 10 shown in FIG. 1 is typical of numerous particle therapy systems, but may also differ from such systems. The exemplary embodiments described in the following may be deployed in conjunction with the particle therapy system described with reference to FIG. 1 and also with other particle therapy systems.

FIG. 2 shows a possible arrangement of a beam outlet and an imaging unit in an irradiation chamber.

The imaging unit includes an X-ray detector 31 and an X-ray emitter 33 arranged opposite to each other on a support arm 35 (e.g., a C-arm). The support arm 35 may be positioned in a flexible manner in the chamber using a robot arm 37 (e.g., using a six-axis elbow-arm robot). The X-ray detector 31 and the X-ray emitter 33 may be used to record X-ray images (e.g., fluoroscopy images) of a patient 39 positioned on a patient couch 41 for the irradiation. For example, the target area to be irradiated or the target volume 43 to be irradiated (e.g., a tumorous organ) may be depicted in the fluoroscopy images.

Alternatively to the embodiment with the support arm, the X-ray detector and the X-ray emitter may also be positioned independently of each other (e.g., using two robot arms). This may facilitate greater flexibility, since there is no rigid support arm arranged between the X-ray emitter and the X-ray detector.

Only either the X-ray detector or the X-ray emitter may be positioned in a movable manner, and the other may be in a static position. For example, the X-ray detector may move, and a movable shutter at the X-ray emitter may provide that the X-ray beams are masked in a different manner.

For the irradiation, a particle beam 47 exits a beam outlet 45 and is directed onto the patient 39. The beam outlet 45 installed in a spatially fixed manner is shown. Alternatively, the beam outlet 45 may be secured to a rotatable gantry so that the beam outlet 45 may be rotated about the patient 39. During the application of the particle beam 47, however, the beam outlet 45 may remain in a fixed position.

The X-ray detector 31 and the X-ray emitter 33 may be positioned independently of the beam outlet 45. During the application of the particle beam 47, the support arm 35 is moved back and forth by the robot arm 37. A series of fluoroscopy images is recorded. A series of digital tomosynthesis images is reconstructed online (e.g., "on the fly" reconstruction) from the series of fluoroscopy images series. In other words, the series of digital tomosynthesis images is reconstructed during the application of the particle beam 47. The recorded fluoroscopy images are forwarded to a computer unit 49, in which reconstruction of the tomosynthesis images takes place.

The movement of the target volume 43 in the series of digital tomosynthesis images may be evaluated (e.g., during the application of the particle beam 47). This evaluation is also performed "on the fly." The information obtained in this way is used to control or regulate the irradiation profile and radiation dose. The evaluation and control of the irradiation profile and the radiation dose are performed in a control unit 51. For example, the particle beam 47 may be switched off as soon as the target volume 43 to be irradiated is no longer in a desired position and may be optionally switched back on again as soon as the target volume 43 to be irradiated is back in the desired position. Alternatively and/or additionally, the particle beam 47 may track a movement of the target volume 43 if the movement of the target volume 43 takes place within certain limits.

The control unit 51 and/or the computer unit 49 for image reconstruction may be implemented in a single computer unit, may be split between different subunits, may be implemented as independent units, or may be in a control unit for the particle therapy system as a whole.

The support arm 35 may be moved in different ways. A simple movement is indicated by a double arrow 55 and corresponds to a pivoting movement. Another option for moving the support arm 35 is a circular or spiral movement, indicated by the spiral 57 or the circle 59. In the case of the last two movements, the X-ray beam axis 36 may execute a precision movement.

Figure 4:
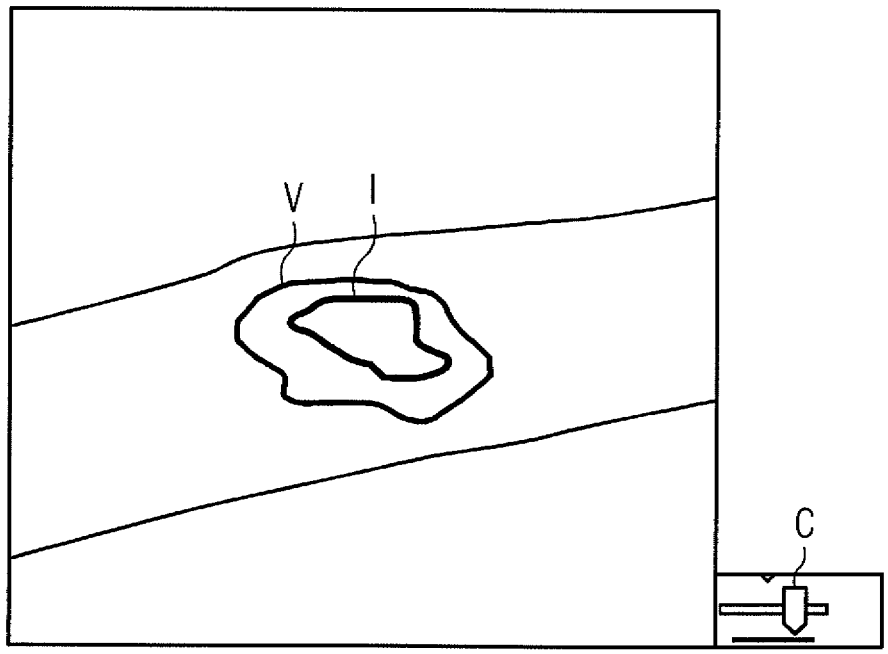

FIGS. 2 and 4 show a target area or a target volume V that may be colored orange, and an isoline or an isosurface I that may be colored blue. The user may change the isoline I of the radiation dose using a user control element C such as, for example, a slider. Changes of this kind may be visualized in real time. The isoline is determined such that the isoline most closely corresponds to the contour of the target area.

A user interface for treatment planning software supports a user in the performance of dose normalization when the radiation dose has been calculated. This may either happen automatically or on the activation of a user control element available to the user as soon as the dose calculation has finished. A normalization element in the treatment planning software offered to the user includes visualization elements and different control elements enabling the user to adjust the dose by changing or visualizing the isoline or isosurface. The user interface tool may accept the dose normalization to be provided.

Different embodiments are described below:
1. Visualization Elements

Visualization elements include one or more two-dimensional presentations of a patient anatomy encompassing contours of the target area and possible risk-prone organs, where the risk is associated with the actual isoline used. In one embodiment, three such presentations are visible showing different sections made rectangular by the patient geometry. The user is provided with a user element that may be used to browse through the different two-dimensional presentations and change the orientation.

In a further embodiment, a 3-dimensional bordered surface of the target area with the risk-prone organs is shown. The risk is again associated with the preset isosurface. The user is provided with simple control elements (e.g., rotation, zoom in, zoom out, and move).

In a further embodiment, there is at least one control element enabling toggling between two-dimensional and three-dimensional depiction or parallel depiction of two-dimensional or three-dimensional visualization.

2. Isoline or Isosurface Alteration Elements

Figure 3:
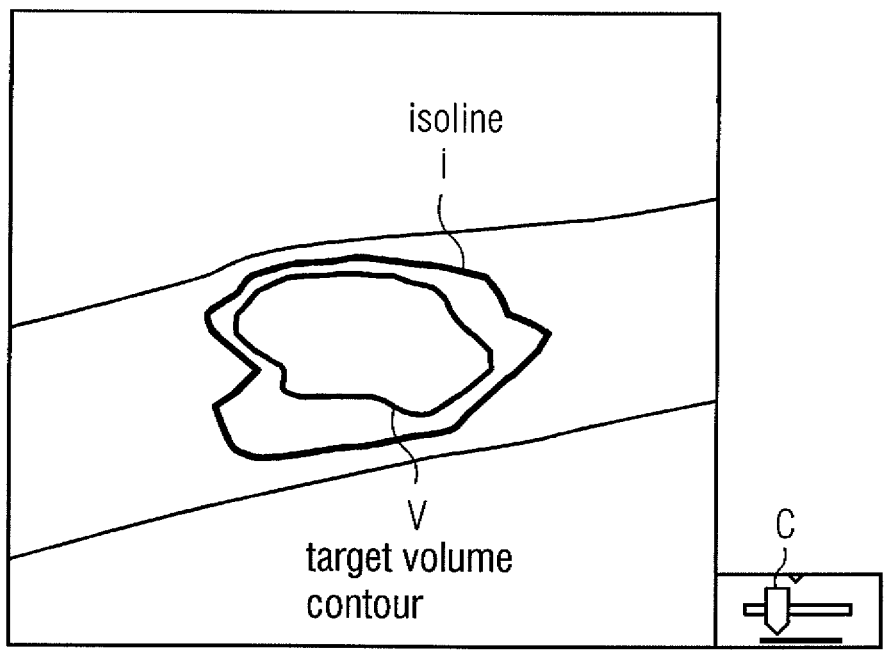
FIGS. 3 and 4 show schematic illustrations for exemplary computer-aided visualization of a radiation dose normalization.

One embodiment provides a slider such as, for example, indicated in FIGS. 3 and 4 as a control element. The slider allows the user to vary the preset isoline or isosurface. The variation options may be restricted by area specifications. When the slider is moved, the corresponding isoline or isosurface is recalculated in real time and changed or visually displayed as changed. The user may manually change the preset isoline or isosurface to a degree, at which the isoline most closely corresponds with the contour of the target area. The inclusion of organs in a risk area is to be prevented.

One embodiment provides that the isoline or isosurface is set to a preconfigured or pre-determined value before the user starts the dose normalization.

In one embodiment, the isoline or isosurface may be automatically determined in that optimum approximation of the isosurface to the target area is calculated.

3. Calculating Isolines or Isosurfaces

The "marching square" or "marching tube" algorithm may be used for this.

4. Automatic Calculation of an Isosurface Optimally Matched to the Target

A further embodiment provides a method for calculating an optimally adjusted isosurface in the target area. The method includes minimizing a cost function expressing a distance between a specified isosurface and the target volume. Different sizes of volume overlapping or contour surface conformance or similarity may be applied as a cost function. The cost function may also include a distribution of organs that are completely or partially risk-prone within the isosurface. The organs introduce a "penalty factor" in the cost function.

5. Dose Normalization Elements

One embodiment provides a control element enabling the user to enter a desired dose value in order to set the isoline appropriately. This enables a suitable isoline or isosurface to be determined manually or automatically as soon as the user determines the specified dose for the selected isoline or isosurface.

A further embodiment provides that the dose value in the control element is initially set by a specification in the treatment plan. In one embodiment, initially, the dose normalization is set at a blank value in the event of there being no dose specification. In this case, the user may enter the desired dose value manually or use a scaling function with respect to the isoline in order to define the desired dose. If sufficient information is available (e.g., the desired dose value for the target area), the dose adjustment may be automatically accepted.

In one embodiment, a user interface tool allows the user to accept the currently defined isoline or isosurface and from this, to normalize the dose again correspondingly.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for regulating a therapeutic beam directed at an object, the method comprising:
    displaying at least one multidimensional image data record encompassing at least one target area of the object;
    determining a treatment beam dosage directed at the at least one target area;
    recording and optionally visualizing an isoline or isosurface dependent on the treatment beam dosage in the at least one multidimensional image data record;
    automatically adjusting the isoline or isosurface such that the isoline or isosurface approximates a contour of the at least one target area as closely as possible or corresponds to the contour;
    adjusting the isoline or isosurface based on a user input via a slider of a user interface; and
    regulating the treatment beam dosage by evaluation of the adjusted isoline or isosurface,
    wherein the automatically adjusting comprises minimizing a cost function that expresses a distance between the isoline or isosurface and the contour of the at least one target area.

2. The method as claimed in claim 1, wherein the regulated treatment beam dosage lies within one or more limit values.

3. The method as claimed in claim 1, wherein determining the treatment beam dosage comprises identifying a preset treatment beam dosage.

4. The method as claimed in claim 1, wherein regulating the treatment beam dosage comprises automatically or manually setting the treatment beam dosage via a user interface.

5. A device for regulating a therapeutic beam directed at an object, the device comprising:
    means for displaying at least one multidimensional image data record encompassing at least one target area of the object;
    means for determining a treatment beam dosage directed at the at least one target area;
    means for recording and optionally means for visualizing an isoline or isosurface dependent upon the treatment beam dosage in the at least one multidimensional image data record;
    means for automatically adjusting the isoline or isosurface such that a cost function that expresses a distance between the isoline or isosurface and a contour of the at least one target area is minimized, and the isoline or isosurface approximates the contour of the at least one target area or corresponds to the contour;
    means for adjusting the isoline or isosurface with the aid of a slider of a user interface; and
    means for regulating the treatment beam dosage by evaluation of the adjusted isoline or isosurface.

6. The device as claimed in claim 5, wherein the regulated treatment beam dosage lies within one or more limit values.

7. The device as claimed in claim 5, wherein the means for determining the treatment beam dosage is operable to identify a preset treatment beam dosage.

8. The device as claimed in claim 5, wherein the means for determining the treatment beam dosage is operable to set the treatment beam dosage automatically or manually via a user interface.

9. In a non-transitory computer readable storage medium that stores program code including instructions executable by a computer for regulating a therapeutic beam directed at an object, the instructions comprising:

displaying at least one multidimensional image data record encompassing at least one target area of the object;

determining a treatment beam dosage directed at the at least one target area;

recording and optionally visualizing an isoline or isosurface dependent upon the treatment beam dosage in the at least one multidimensional image data record;

adjusting the isoline or isosurface such that the isoline or isosurface approximates a contour of the at least one target area or corresponds to the contour, wherein the adjusting comprises adjusting the isoline or isosurface with the aid of a slider of a user interface; and regulating the treatment beam dosage by evaluation of the adjusted isoline or isosurface.

10. A device for regulating a therapeutic beam directed at an object, the device comprising:

a display device operable to display at least one multidimensional image data record encompassing at least one target area of the object; and a control unit in communication with the display, the control unit configured to:

determine a treatment beam dosage directed at the at least one target area;

record and optionally visualize an isoline or isosurface dependent upon the treatment beam dosage in the at least one multidimensional image data record;

adjust the isoline or isosurface such that the isoline or isosurface approximates a contour of the at least one target area or corresponds to the contour, the adjustment of the isoline or isosurface being based on a user input via a slider of a user interface; and regulate the treatment beam dosage by evaluation of the adjusted isoline or isosurface.

11. The device as claimed in claim 10, wherein the regulated treatment beam dosage lies within one or more limit values.

12. The device as claimed in claim 10, wherein the control unit is further configured to identify a preset treatment beam dosage such that the treatment beam dosage directed at the at least one target area is determined.

13. The device as claimed in claim 10, wherein the control unit is further configured to set the treatment beam dosage automatically or manually via a user interface.

* * * * *